United States Patent [19]

Marschner et al.

[11] Patent Number: 5,585,518

[45] Date of Patent: Dec. 17, 1996

[54] HYDROXYPHENYLUREAS

[75] Inventors: Claus Marschner, Speyer; Knut Kessel, Mannheim; Manfred Patsch, Wachenheim, all of Germany

[73] Assignee: BASF Aktiengesellschaft, Ludwigshafen, Germany

[21] Appl. No.: 419,282

[22] Filed: Apr. 10, 1995

[30] Foreign Application Priority Data

Apr. 16, 1994 [DE] Germany .................. 44 13 265.4

[51] Int. Cl.$^6$ .................................................. C07C 275/06
[52] U.S. Cl. ........................... 564/49; 564/50; 564/52; 544/58.2; 544/390
[58] Field of Search ................. 564/49, 50, 52; 544/58.2, 390

[56] References Cited

U.S. PATENT DOCUMENTS 4,797,419  1/1989  Moos et al. .................. 514/588

FOREIGN PATENT DOCUMENTS

0592980A2  4/1994  European Pat. Off. .
0592980A3  4/1994  European Pat. Off. .

OTHER PUBLICATIONS

CA110:147876p Method of treating . . . preparation. Moss et al., p. 90, 1989.

Journal Fuer Praktische Chemie, Bd. 48, 1983, Leipzig, DE, Seiten 425–446, R. Schmitt: "Ueber die Einwirkung con Chlorkohleonxyd auf Pikraminsaeure".

B. Hadjieva, et al., "1–(2–Hydroxyaryl)–3–(2–Hydroxyethyl)–and 3,3–Dialkyl Ureas: Synthesis, Herbicidal and Plant Growth–Regulating Activities", Comptes Rendus de l'Academie Bulgare des Sciences, vol. 41, No. 9, 1988, pp. 113–116.

*Primary Examiner*—Joseph McKane
*Attorney, Agent, or Firm*—Oblon, Spivak, McClelland, Maier & Neustadt, P.C.

[57] ABSTRACT

Useful ureas have the formula

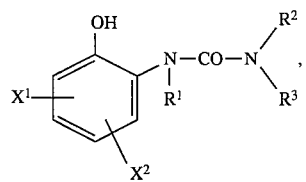

5 Claims, No Drawings

HYDROXYPHENYLUREAS

The present invention relates to ureas of the formula I

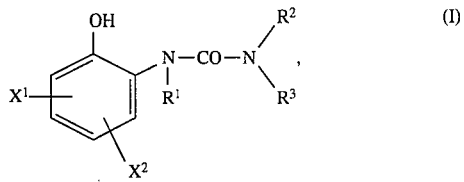

where $X^1$ is nitro or amino, $X^2$ is nitro, amino, hydroxysulfonyl, sulfamoyl, mono- or di($C_1$–$C_4$-alkyl)sulfamoyl or a radical of the formula —S(O)$_n$—Y, where n is 0 or 2 and Y is vinyl or a radical of the formula $C_2H_4$—Q, where Q is hydroxyl or contains an alkali-detachable group, $R^1$ is hydrogen, $C_1$–$C_6$-alkyl with or without substitution and with or without interruption by 1 or 2 oxygen atoms in ether function or by imino or $C_1$–$C_4$-alkylimino groups, or $C_3$–$C_4$-alkenyl, $R^2$ and $R^3$ are independently of each other $C_1$–$C_6$-alkyl with or without substitution and with or without interruption by 1 or 2 oxygen atoms in ether function or imino or $C_1$–$C_4$-alkylimino groups, or substituted or unsubstituted phenyl, or else $R^2$ may also be hydrogen or a radical of the formula

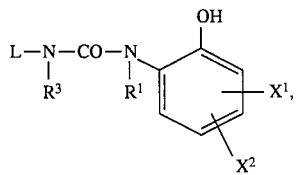

where L is $C_2$–$C_8$-alkylene or phenylene and $R^1$, $R^3$, $X^1$ and $X^2$ are each as defined above, or else $R^2$ and $R^3$ are together a radical of the formula (—$C_2H_4$)$_2$N—$R^1$, where $R^1$ is as defined above, with the proviso that a) compounds of the formula

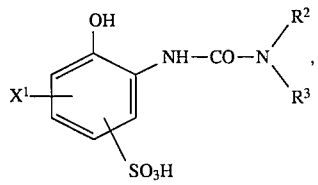

where $X^1$ is nitro or amino and $R^2$ and $R^3$ are either or both $C_1$–$C_6$-alkyl with or without substitution by the radical —S(O)$_n$—Y, where n and Y are each as defined above, and with or without interruption by 1 or 2 oxygen atoms in ether function or by imino or $C_1$–$C_4$-alkylimino groups, and b) compounds of the formula

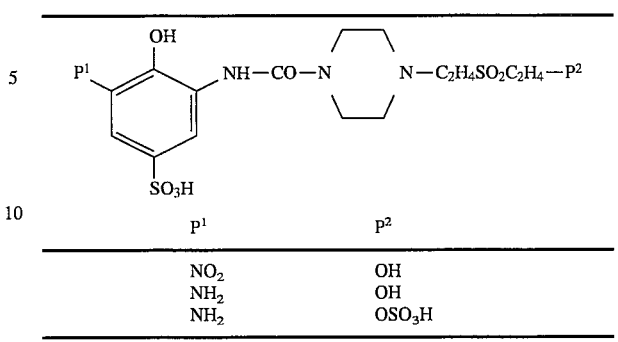

| $P^1$ | $P^2$ |
|---|---|
| $NO_2$ | OH |
| $NH_2$ | OH |
| $NH_2$ | $OSO_3H$ | are excluded,
and to a process for preparing them.

Earlier Patent Application EP-A-592 980 discloses ureas which have been excluded from the abovementioned formula I.

Furthermore, Comptes rendus de l'Académie bulgare des Sciences 41 (1988), 113–116 describes hydroxyphenylureas containing a nitro group in the phenyl ring.

It is an object of the present invention to provide novel hydroxyphenylureas which shall be advantageous for synthesizing metal complex dyes.

Any alkyl, alkenyl or alkylene group appearing in the abovementioned formula may be straight-chain or branched.

Any substituted alkyl appearing in the abovementioned formula may have as substituents for example hydroxyl, amino, cyano, carboxyl, hydroxysulfonyl, sulfato, carbamoyl, mono- or di($C_1$–$C_4$-alkyl)carbamoyl, piperazino, N-($C_1$–$C_4$-alkyl)piperazino, thiomorpholine S,S-dioxide or a radical of the formula —S(O)$_n$—Y, where n and Y are each as defined above. The number of substituents in substituted alkyl is generally 1 or 2 and the substituents may be identical or different.

Substituted phenyl appearing in the abovementioned formula may have as substituents for example $C_1$–$C_4$-alkyl, $C_1$–$C_4$-alkoxy, halogen, nitro, amino, mono- or di($C_1$–$C_4$-alkyl)amino, $C_1$–$C_4$-alkanoylamino, benzylamino, carboxyl, carbamoyl, mono- or di($C_1$–$C_4$-alkyl)carbamoyl, hydroxysulfonyl or a radical of the formula —S(O)$_n$—Y, wherein n and Y are each as defined above. The number of substituents in substituted phenyl is generally from 1 to 3 and the substituents may be identical or different.

Q is hydroxyl or an alkali-detachable group. Such groups include for example chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, substituted or unsubstituted phenylsulfonyloxy, $C_1$–$C_4$-alkanoyloxy, di($C_1$–$C_4$-alkyl)amino or a radical of the formula

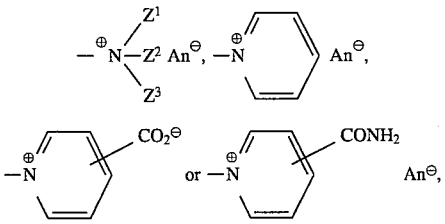

where $Z^1$, $Z^2$ and $Z^3$ are each independently of the others $C_1$–$C_4$-alkyl or benzyl and An$^\ominus$ is in each case one equivalent of an anion. Suitable anions include for example fluoride, chloride, bromide, iodide, mono-, di- or trichloroacetate, methanesulfonate, benzenesulfonate or 2- or 4-methylbenzenesulfonate.

$R^1$, $R^2$, $R^3$, $Z^1$, $Z^2$ and $Z^3$ are each for example methyl, ethyl, propyl, isopropyl, butyl, isobutyl, sec-butyl or tert-butyl.

$R^1$, $R^2$ and $R^3$ may each also be for example pentyl, isopentyl, neopentyl, tert-pentyl, hexyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 4-methoxybutyl, 2- or 4-ethoxybutyl, 3,6-dioxaheptyl, 3,6-dioxaoctyl, 3-azapentyl, 3-methyl-3-azapentyl, 2-hydroxyethyl, 2- or 3-hydroxypropyl, 2- or 4-hydroxybutyl, 5-hydroxypentyl, 6-hydroxyhexyl, 2-aminosthyl, 2- or 3-aminopropyl, 2- or 4-aminobutyl, 5-aminopentyl, 6-aminohexyl, cyanomethyl, 2-cyanoethyl, 2- or 3-cyanopropyl, 2- or 4-cyanobutyl, 5-cyanopentyl, 6-cyanohexyl, carbonylmethyl, 2-carboxyethyl, 2- or 3-carboxypropyl, 2- or 4-carboxybutyl, 5-carboxypentyl, 6-carboxyhexyl, 2-hydroxysulfonylethyl, 2- or 3-hydroxysulfonylpropyl, 2- or 4-hydroxysulfonylbutyl, 5-hydroxysulfonylpentyl, 6-hydroxysulfonylhexyl, 2-sulfatoethyl, 2- or 3-sulfatopropyl, 2- or 4-sulfatobutyl, 5-sulfatopentyl, 6-sulfatohexyl, carbamoylmethyl, 2-carbamoylethyl, 2- or 3-carbamoylpropyl, 2- or 4-carbamoylbutyl, 5-carbamoylpentyl, 6-carbamoylhexyl, mono- or dimethylcarbamoylmethyl, mono- or diethylcarbamoylmethyl, 2-(mono- or dimethylcarbamoyl)ethyl, 2-(mono- or diethylcarbamoyl)ethyl, 2- or 3-(mono- or dimethylcarbamoyl)propyl, 2- or 3-(mono- or diethytcarbamoyl)propyl, 2- or 4-(mono- or dimethylcarbamoyl)butyl, 2- or 4-(mono- or diethylcarbamoyl)butyl, 2-(piperazin-1-yl)ethyl, 2- or 3-(piperazin-1-yl)propyl, 2- or 4-(piperazin-1-yl)butyl, 2-(4-methylpiperazin-1-yl)ethyl, 2- or 3-(4-methylpiperazin-1-yl)propyl, 2- or 4-(4-methylpiperazin-1-yl)butyl, 2-(4-thiomorpholinyl S,S-dioxide)ethyl, 2- or 3-(4-thiomorpholinyl S,S-dioxide)propyl, 2- or 4-(4-thiomorpholinyl S,S-dioxide)butyl or a radical of the formula —$(CH_2)_2$—S—Y, —$(CH_2)_2$—$SO_2$—Y, —$(CH_2)_3$—S—Y, —$CH_2$—$CH(CH_3)$—S—Y, —$(CH_2)_3$—$SO_2$—Y, —$CH_2$—$CH(CH_3)$—$SO_2$—Y, —$(CH_2)_4$—S—Y, $(CH_2)_4$—$SO_2$—Y, $(CH_2)_2O(CH_2)_2$—S—Y, $(CH_2)_2O(CH_2)_2$—$SO_2$—Y, $(CH_2)_2NH(CH_2)_2$—S—Y, $(CH_2)_2NH(CH_2)_2$—$SO_2$—Y, $$(CH_2)_2\underset{\underset{CH_3}{|}}{N}(CH_2)_2-S-Y, \quad (CH_2)_2\underset{\underset{CH_3}{|}}{N}(CH_2)_2-SO_2-Y,$$

$(CH_2)_2O(CH_2)_2O(CH_2)_2$—S—Y,
$(CH_2)_2O(CH_2)_2O(CH_2)_2$—$SO_2$—Y,
$(CH_2)_2NH(CH_2)_2NH_2(CH_2)_2$—S—Y,
$(CH_2)_2NH(CH_2)_2NH(CH_2)_2$—$SO_2$—Y, $$(CH_2)_2\underset{\underset{CH_3}{|}}{N}(CH_2)_2\underset{\underset{CH_3}{|}}{N}(CH_2)_2-S-Y \text{ or}$$

$$(CH_2)_2\underset{\underset{CH_3}{|}}{N}(CH_2)_2\underset{\underset{CH_3}{|}}{N}(CH_2)_2-SO_2-Y,$$

where Y is in each case as defined above.

$R^1$ may also be for example allyl or methallyl.

$R^2$ and $R^3$ may each also be for example phenyl, 2-, 3- or 4-methylphenyl, 2,4-dimethylphenyl, 2-, 3- or 4-methoxyphenyl, 2-, 3- or 4-chlorophenyl, 2-, 3- or 4-aminophenyl, 2-, 3- or 4-(mono- or dimethylamino)phenyl, 2-, 3- or 4-(mono- or diethylamino)phenyl, 2-, 3- or 4-formylaminophenyl, 2-, 3- or 4-acetylaminophenyl, 2-, 3- or 4-propionylaminophenyl, 2-, 3- or 4-butyrylaminophenyl, 2-, 3- or 4-isobutyrylaminophenyl, 2-, 3- or 4-carboxyphenyl, 2-, 3- or 4-carbamoylphenyl, 2-, 3- or 4-(mono- or dimethylcarbamoyl)-phenyl, 2-, 3- or 4-(mono- or diethylcarbamoylphenyl), 2-, 3- or 4-hydroxysulfonylphenyl or a radical of the formula where Y is in each case as defined above.

$X^2$ is for example mono- or dimethylsulfamoyl, mono- or diethylsulfamoyl, mono- or dipropylsulfamoyl, mono- or diisopropylsulfamoyl, mono- or dibutylsulfamoyl or N-methyl-N-ethylsulfamoyl.

L is for example $(CH_2)_2$, $(CH_2)_3$, $(CH_2)_4$, $(CH_2)_5$, $(CH_2)_6$, $(CH_2)_7$, $(CH_2)_8$, $CH(CH_3)CH_2$, $CH(CH_3)CH(CH_3)$ or 1,2-, 1,3- or 1,4-phenylene.

Preference is given to ureas of the formula I where $X^2$ is nitro, amino, hydroxysulfonyl or a radical of the formula —$SO_2$—Y, where Y is as defined above, hydroxysulfonyl or a radical of the formula —$SO_2Y$ being particularly noteworthy.

Preference is further given to ureas of the formula I where $R^1$ is hydrogen or unsubstituted or hydroxysulfonyl-, hydroxyl- or sulfato-substituted $C_1$–$C_6$-alkyl, hydrogen being particularly noteworthy.

Preference is further given to ureas of the formula I where $R^2$ is hydrogen or $C_1$–$C_6$-alkyl, in particular hydrogen, and $R^3$ is $C_1$–$C_6$-alkyl with or without substitution by amino, hydroxyl, hydroxysulfonyl, sulfato or a radical of the formula —$SO_2$—Y, where Y is as defined above, and with or without interruption by an oxygen atom in ether function or by an imino group, or is phenyl with or without substitution by amino, mono-$C_1$–$C_4$-alkylamino, $C_1$–$C_4$-alkanoylamino, benzoylamino, carboxyl, hydroxysulfonyl or a radical of the formula —$SO_2$—Y, where Y is as defined above, or $R^2$ and $R^3$ are together a radical of the formula (—$C_2H_4)_2N$—$R^1$, where $R^1$ is as defined above.

Preference is further given to ureas of the formula I where

L is $C_2$–$C_4$-alkylene or phenylene.

The ureas of the formula I can be prepared by methods known per se, as described for example in EP-A-592 980, for instance by reacting a benzoxazolone of the formula II (II)

where $X^1$, $X^2$ and $R^1$ are each as defined above, with an amine of the formula III (III)

where $R^2$ and $R^3$ are each as defined above.

The novel ureas of the formula I are useful intermediates for the synthesis of metal complex dyes, especially of reactive dyes based on formazans (see for example EP-A-592 980).

The Examples which follow illustrate the invention.

EXAMPLES

EXAMPLE 1 a) To 160 g of sodium hydroxide in 1.5 l of water were added with cooling at from 20° to 40° C. 232 g of 3-amino-4-hydroxy-5-nitrobenzenesulfonic acid. The reaction mixture was cooled down to 0°–10° C., and then 182 g of phosgene were passed in over 8 hours during which the pH was maintained within the range from 7.5 to 8.5 with 150 g of 50% strength by weight sodium hydroxide solution. The mixture was subsequently stirred for one hour and then excess phosgene was blown out with nitrogen. The pH was set to 7 with 200 g of concentrated hydrochloric acid. To the resulting 7-nitrobenzoxazol-2-one-5-sulfonic acid (sodium salt) were added 67 g of ethanolamine and the pH was adjusted to 7 with 164 g of concentrated hydrochloric acid. The mixture was heated to 60° C. and stirred at that temperature for 6.5 hours. On completion of conversion (TLC), the pH was adjusted to 1.5 with concentrated hydrochloric acid, and the precipitated product was filtered off with suction and dried at from 70° to 80° C. under reduced pressure to leave 289 g of the compound of the formula

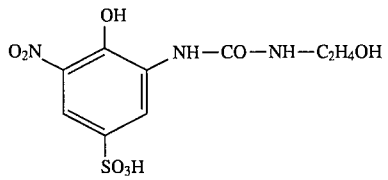

$^1$H-NMR [D$^6$-DMSO]: δ=3.2, 3.4 (both CH$_2$) 4.7 (OH), 7.7, 8.2 (aromatics H) 8.1, 8.9 (NH)

b) 280 g of the nitro compound obtained under a) were dissolved in 3 l of water. 5 g of palladium catalyst (10% by weight on carbon) were added, and the hydrogenation was carried out at from 35° to 40° C. After the uptake of hydrogen had ceased, the catalyst was filtered off and the mother liquor was evaporated to dryness, leaving 250 g of the compound of the formula

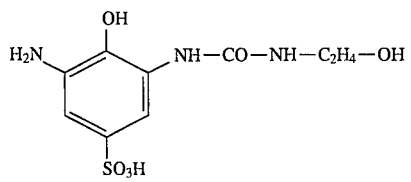

$^1$H-NMR [D$^6$-DMSO]:δ=3.2, 3.4 (both CH$_2$) 4.7 (OH), 7.35, 7.50 (aromatics H) 7.10, 8.70 (NH).

The method of Example 1a) also yields the compounds listed in Table 1.

TABLE 1

| Ex. No. | W$^1$ | W$^2$ | W$^3$ |
|---|---|---|---|
| 2 | NO$_2$ | SO$_3$H | N(C$_2$H$_5$)$_2$ |
| 3 | NO$_2$ | SO$_3$H | N(CH$_3$)CH$_2$CH$_2$OH |
| 4 | NO$_2$ | SO$_3$H | N(CH$_2$CH$_2$OH)2 |
| 5 | NO$_2$ | SO$_3$H | piperazine (N⌒NH) |
| 6 | NO$_2$ | SO$_3$H | NHCH$_2$CH$_2$NH$_2$ |
| 7 | NO$_2$ | SO$_3$H | HNCH$_2$CH$_2$NHCH$_2$CH$_2$OH |
| 8 | NO$_2$ | SO$_3$H | N⌒SO$_2$ (thiomorpholine dioxide) |
| 9 | NO$_2$ | SO$_3$H | HNCH$_2$CH$_2$SO$_3$H |
| 10 | NO$_2$ | SO$_3$H | HNCH$_2$CO$_2$H |
| 11 | NO$_2$ | SO$_3$H | HN-phenyl |
| 12 | NO$_2$ | SO$_3$H | HN-C$_6$H$_4$-SO$_3$H |
| 13 | NO$_2$ | SO$_3$H | HN-C$_6$H$_4$-CO$_2$H (meta) |
| 14 | NO$_2$ | SO$_3$H | HN-C$_6$H$_4$-NH-COCH$_3$ |
| 15 | NO$_2$ | SO$_3$H | HN-C$_6$H$_3$(SO$_3$H)(NHCH$_3$) |
| 16 | NO$_2$ | SO$_3$H | HN-C$_6$H$_2$(OH)(NO$_2$)(SO$_3$H) |
| 17 | NO$_2$ | SO$_3$H | HNCH$_2$CH$_2$N⌒NH (piperazinyl) |

Table 1 structure:

OH on aromatic ring with W$^1$, W$^2$, and HN—CO—W$^3$ substituents.

Catalytic hydrogenation of the abovementioned nitro compounds as per Example 1b yields the corresponding amino compounds (W$^1$=NH$_2$).

EXAMPLE 18 a) Example 1a was repeated with the 3-amino-4-hydroxy-5-nitrobenzenesulfonic acid replaced by 232 g of the isomeric 2-hydroxy-3-amino-5-nitrobenzenesulfonic acid, affording 365 g of the compound of the formula

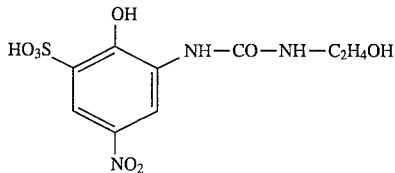

b) The nitro compound obtained under a) was reduced as per Example 1b, affording, after drying at from 30° to 4° C., 295 g of the compound of the formula

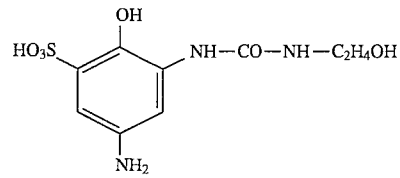

The method of Example 18a), applied to appropriately substituted o-aminohydroxybenzene derivatives, can be used to obtain the compounds listed below in Table 2.

Catalytic hydrogenation of the nitro compounds listed in Table 2 as per Example 1b) gives the corresponding amino compounds.

TABLE 2

| Ex. No. | $W^1$ | $W^2$ | $W^3$ |
|---|---|---|---|
| 19 | $SO_3H$ | $NO_2$ | $N(CH_3)CH_2CH_2SO_3H$ |
| 20 | $SO_3H$ | $NO_2$ | piperazinyl—$C_2H_4OH$ |
| 21 | $SO_3H$ | $NO_2$ | $HNCH_2CH_2NH_2$ |
| 22 | $SO_3H$ | $NO_2$ | HN—C$_6$H$_4$—$SO_3H$ |
| 23 | $NO_2$ | $SO_2CH_2CH_2OH$ | $HNCH_2CH_2OH$ |
| 24 | $NO_2$ | $SO_2CH_2CH_2OH$ | $N(C_2H_5)_2$ |
| 25 | $NO_2$ | $SO_2CH_2CH_2OH$ | $HNCH_2CH_2NH_2$ |
| 26 | $NO_2$ | $SO_2CH_2CH_2OH$ | $HNCH_2CH_2NHCH_2CH_2OH$ |
| 27 | $NO_2$ | $SO_2CH_2CH_2OH$ | $HNCH_2CH_2SO_2CH_2CH_2OH$ |
| 28 | $NO_2$ | $SO_2CH_2CH_2OH$ | HN—C$_6$H$_4$—$SO_2CH_2CH_2OH$ |
| 29 | $NO_2$ | $SO_2CH_2CH_2OH$ | HN—C$_6$H$_3$($NHCH_3$)—$SO_3H$ |
| 30 | $NO_2$ | $SO_2CH_2CH_2OH$ | $HNCH_2CH_2N$-piperazinyl-NH |

EXAMPLE 31 a) Example 1a) was repeated except that, after the phosgene had been blown out, the pH was increased to 8.0–8.5 and 148 g of hydroxymethanesulfonic acid were added. The mixture was subsequently stirred at from 60° to 80° C. for 4 hours until alkylation was complete (TLC), at which point 153 g of 2-aminoethyl 2'-hydroxyethyl sulfone were added, and the rest of the procedure was carried out as in Example 1a), affording 383 g of the compound of the formula

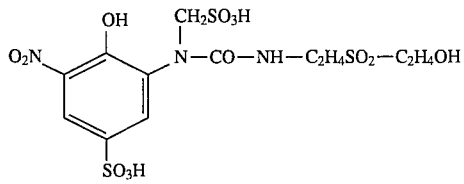

$^1$H-NMR [D$^6$-DMSO]: δ=3.10, 3.20, 3.30, 3.40, 3.80 (in each case CH$_2$), 4.20 (OH) 6.50 (NH) 7.50, 8.00 (aromatics H).

b) 306 g of the nitro compound obtained under a) were dissolved in 3 l of water. 5 g of palladium catalyst (10% by weight on carbon) were added, and hydrogenation was carried out at from 35° to 40° C. After the uptake of hydrogen had ceased, the catalyst was filtered off and the mother liquor was evaporated to dryness, leaving 250 g of the compound of the formula

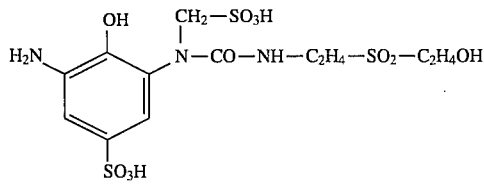

$^1$H-NMR [D$^6$-DMSO]: δ=2.40, 2.90, 3.15, 3.40, 3.75 (in each case CH$_2$) 4.50 (OH, NH2), 6.40 (NH) 6.60, 6.90 (aromatics H).

c) 280 g of the urea obtained under b) were added to 1120 g of chlorosulfonic acid at from 10° to 15° C. with ice cooling, and the reaction mixture was stirred at room temperature for about 12 hours. Following complete conversion (TLC), the reaction mixture was poured onto 4 l of ice, and the precipitated product was filtered off with suction, washed neutral with water and dried under reduced pressure at from 30° to 40° C. to leave 302 g of the compound of the formula

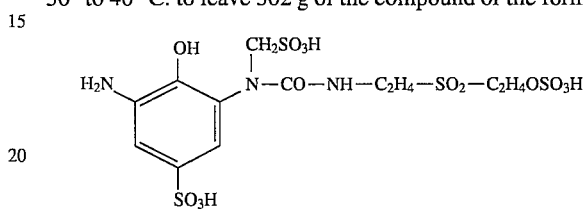

which can be used without further purification for dye syntheses.

Repeating Example 31 with the hydroxymethanesulfonic acid replaced by 1.1 mol of an alkylating agent, such as dimethyl sulfate, methyl p-toluenesulfonate, ethyl iodide, ethylene oxide, 1,4-butanesultone or allyl bromide, stirring at from 60° to 80° C. for 4 hours until conversion is complete (TLC), then adding 1.1 mol of an alkylamine or arylamine and continuing as described in Example 31, yield through the use of appropriate o-aminohydroxybenzene derivatives the ureas listed in the following table

TABLE 3

| Ex. No. | W$^1$ | W$^2$ | W$^3$ | W$^4$ |
|---|---|---|---|---|
| 32 | NH$_2$ | SO$_3$H | CH$_3$ | HNCH$_2$CH$_2$OH |
| 33 | NH$_2$ | SO$_3$H | CH$_3$ | HNCH$_2$CH$_2$SO$_2$CH$_2$CH$_2$Cl |
| 34 | NH$_2$ | SO$_3$H | CH$_3$ | HN—C$_6$H$_4$—SO$_3$H |
| 35 | NH$_2$ | SO$_3$H | CH$_2$SO$_3$H | HNCH$_2$CH$_2$OH |
| 36 | NH$_2$ | SO$_3$H | CH$_3$ | HNCH$_2$CH$_2$SO$_2$CH$_2$CH$_2$OSO$_3$H |
| 37 | NH$_2$ | SO$_3$H | CH$_2$CH$_2$OH | HNCH$_2$CH$_2$OH |
| 38 | NH$_2$ | SO$_3$H | CH$_2$CH$_2$OSO$_3$H | HNCH$_2$CH$_2$SO$_2$CH$_2$CH$_2$OSO$_3$H |
| 39 | NH$_2$ | SO$_2$CH$_2$CH$_2$OH | CH$_2$CH$_2$OH | NHC$_2$H$_5$ |
| 40 | NH$_2$ | SO$_2$CH$_2$CH$_2$OSO$_3$H | CH$_3$ | NHCH$_2$CH$_2$SO$_2$CH$_2$CH$_2$OSO$_3$H |
| 41 | NH$_2$ | SO$_2$CH$_2$CH$_2$OSO$_3$H | CH$_2$SO$_3$H | NHCH$_2$CH$_2$SO$_2$CH$_2$CH$_2$OSO$_3$H |
| 42 | NH$_2$ | SO$_2$CH$_2$CH$_2$OSO$_3$H | CH$_2$CH$_2$OSO$_3$H | NHCH$_2$CH$_2$SO$_2$CH$_2$CH$_2$OSO$_3$H |
| 43 | NH$_2$ | SO$_2$CH$_2$CH$_2$OSO$_3$H | (CH$_2$)$_4$OSO$_3$H | NHCH$_2$CH$_2$NHCH$_2$CH$_2$OSO$_3$H |
| 44 | NH$_2$ | SO$_2$CH$_2$CH$_2$OSO$_3$H | CH$_2$CH=CH$_2$ | NHCH$_2$CH$_2$NHCH$_2$CH$_2$OSO$_3$H |

TABLE 3-continued

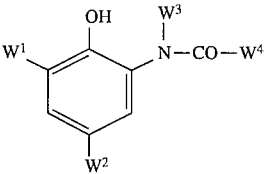

| Ex. No. | W¹ | W² | W³ | W⁴ |
|---|---|---|---|---|
| 45 | $NH_2$ | $SO_3H$ | $CH_2CH_2OSO_3H$ | 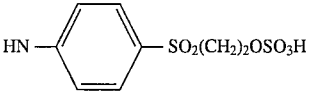 |
| 46 | $NH_2$ | $SO_2CH_2CH_2OSO_3H$ | $CH_2CH_2OSO_3H$ | 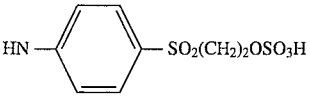 |

EXAMPLE 47

Example 1a) was repeated with the ethanolamine replaced by 30 g (0.5 mol) of ethylenediamine, affording 310 g of the compound of the formula

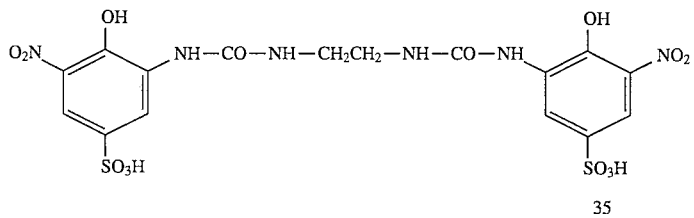

$^1$H-NMR [D$^6$-DMSO]: δ=3.4 (CH$_2$) 7.7, 8.2 (aromatics H) 7.7, 8.6 (NH).

The method of Example 47 can also be used to obtain the compounds listed in Table 4.

Catalytic hydrogenation over palladium/carbon gives the corresponding amino compounds (W¹=NH$_2$).

TABLE 4

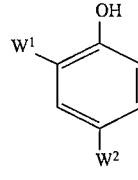

| Ex. No. | W¹ | W² | W³ | B |
|---|---|---|---|---|
| 48 | $NO_2$ | $SO_3H$ | H | $NH-CH_2CH_2CH_2-NH$ |
| 49 | $NO_2$ | $SO_3H$ | H | 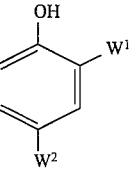 |
| 50 | $NO_2$ | $SO_3H$ | H | $HN-CH_2CH_2-N$<br>$\quad\quad\quad\quad\quad\quad\;\;\;\|$<br>$\quad\quad\quad\quad\quad\quad\;\;\;CH_2CH_2OH$ |
| 51 | $NO_2$ | $SO_2(CH_2)_2OH$ | H | $HN-CH_2CH_2-NH$ |
| 52 | $NO_2$ | $SO_2(CH_2)_2OH$ | H | $HN-CH_2CH_2-N$<br>$\quad\quad\quad\quad\quad\quad\;\;\;\|$<br>$\quad\quad\quad\quad\quad\quad\;\;\;CH_2CH_2OH$ |
| 53 | $NO_2$ | $SO_3H$ | $CH_2SO_3H$ | $HN-CH_2CH_2-NH$ |
| 54 | $NO_2$ | $SO_2(CH_2)_2OH$ | $CH_2SO_3H$ | $HN-CH_2CH_2-NH$ |

We claim:
1. Ureas of the formula I

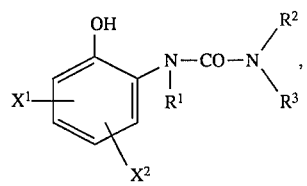

where
- $X^1$ is nitro or amino,
- $X^2$ is amino, hydroxysulfonyl, sulfamoyl, mono- or di($C_1$–$C_4$-alkyl)sulfamoyl or a radical of the formula —$S(O)_n$—Y, where n is 0 or 2 and Y is vinyl or a radical of the formula $C_2H_4$—Q, where Q is hydroxyl or contains an alkali-detachable group,
- $R^1$ is hydrogen, $C_1$–$C_6$-alkyl with or without substitution and with or without interruption by 1 or 2 oxygen atoms in ether function or by imino or $C_1$–$C_4$-alkylimino groups, or $C_3$–$C_4$-alkenyl,
- $R^2$ and $R^3$ are independently of each other $C_1$–$C_6$-alkyl with or without substitution and with or without interruption by 1 or 2 oxygen atoms in ether function or imino or $C_1$–$C_4$-alkylimino groups, or substituted or unsubstituted phenyl, or else $R^2$ may also be hydrogen or a radical of the formula

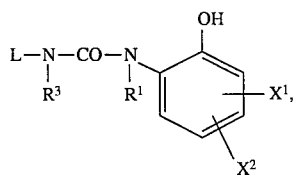

where L is $C_2$–$C_8$-alkylene or phenylene and $R^1$, $R^3$, $X^1$ and $X^2$ are each as defined above, or else $R^2$ and $R^3$ are together a radical of the formula (—$C_2H_4$)$_2$N—$R^1$, where $R^1$ is as defined above, with the proviso that
a) compounds of the formula

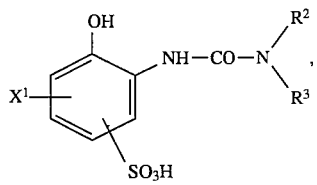

where $X^1$ is nitro or amino and $R^2$ and $R^3$ are either or both $C_1$–$C_6$-alkyl with or without substitution by the radical —$S(O)_n$—Y, where n and Y are each as defined above, and with or without interruption by 1 or 2 oxygen atoms in ether function or by imino or $C_1$–$C_4$-alkylimino groups, and b) compounds of the formula

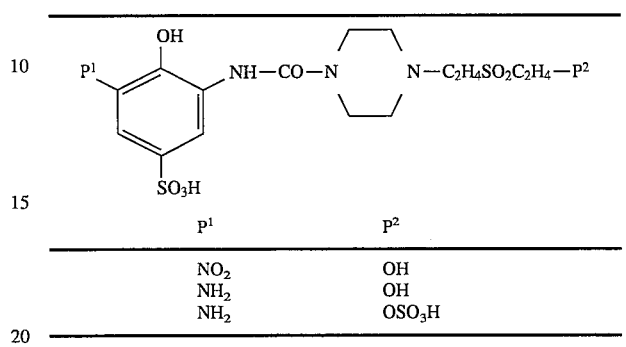

| $P^1$ | $P^2$ |
|---|---|
| $NO_2$ | OH |
| $NH_2$ | OH |
| $NH_2$ | $OSO_3H$ | are excluded.

2. Ureas as claimed in claim 1, wherein
$X^2$ is amino, hydroxysulfonyl or a radical of the formula —$SO_2$—Y, where Y is as defined in claim 1.

3. Ureas as claimed in claim 1, wherein
$R^1$ is hydrogen or unsubstituted or hydroxysulfonyl-, hydroxyl - or sulfato-substituted $C_1$–$C_6$-alkyl.

4. Ureas as claimed in claim 1, wherein
$R^2$ is hydrogen or $C_1$–$C_6$-alkyl, and
$R^3$ is $C_1$–$C_6$-alkyl with or without substitution by amino, hydroxyl, hydroxysulfonyl, sulfato or a radical of the formula —$SO_2$—Y, where Y is as defined in claim 1, and with or without interruption by an oxygen atom in ether funtion or by an imino group, or is phenyl with or without substitution by amino, mono—$C_1$–$C_4$-alkylamino, $C_1$–$C_4$-alkanoylamino, benzoylamino, carboxyl, hydroxysulfonyl or a radical of the formula —$SO_2$—Y, where Y is as defined in claim 1, or $R^2$ and $R^3$ are together a radical of the formula (—$C_2H_4$)$_2$N—$R^1$, where $R^1$ is as defined in claim 1.

5. Ureas as claimed in claim 1, wherein
L is $C_2$–$C_4$-alkylene or phenylene.

* * * * *